United States Patent [19]

Hussain

[11] Patent Number: 5,077,334

[45] Date of Patent: Dec. 31, 1991

[54] FLAME-RETARDED FORMULATIONS OF THERMOPLASTICS AND DECABROMODIPHENYLETHANE

[75] Inventor: Saadat Hussain, Baton Rouge, La.

[73] Assignee: Ethyl Corporation, Richmond, Va.

[21] Appl. No.: 637,818

[22] Filed: Jan. 7, 1991

Related U.S. Application Data

[60] Division of Ser. No. 387,952, Jul. 31, 1989, which is a continuation-in-part of Ser. No. 205,728, Jun. 13, 1988, abandoned.

[51] Int. Cl.$^5$ .............................................. C08K 5/03
[52] U.S. Cl. ................................................... 524/469
[58] Field of Search ......................................... 524/469

[56] References Cited

FOREIGN PATENT DOCUMENTS 56-070059  6/1981  Japan .

Primary Examiner—Paul R. Michl
Assistant Examiner—Tae H. Yoon
Attorney, Agent, or Firm—E. E. Spielman, Jr.

[57] ABSTRACT

This invention relates to a process for preparing a product which is predominant in decabromodiphenyl alkane. The process comprises: forming a stirrable reaction mass by adding a solution containing methylene bromide and diphenylalkane to a reaction vessel containing elemental bromine ($Br_2$) and a bromination catalyst; maintaining the reaction mass for a period of time sufficient to achieve perbromination of substantially all of said diphenylalkane; and recovering from the reaction mass the product which is predominant is decabromodiphenyl alkane.

12 Claims, No Drawings

FLAME-RETARDED FORMULATIONS OF THERMOPLASTICS AND DECABROMODIPHENYLETHANE

CROSS-REFERENCE TO RELATED APPLICATION

This application is a division of co-pending application Ser. No. 387,952, filed July 31, 1989, now pending which in turn is a continuation-in-part of application Ser. No. 205,728, filed June 13, 1988, now abandoned.

This application is a continuation-in-part of co-pending application Ser. No. 205,728, filed June 13, 1988.

This invention relates to a process for preparing a product predominant in decabromodiphenyl alkane.

Polybromodiphenylalkanes, e.g. decabromodiphenyl ethane, are known flame retardants for use in polyolefin and in polystyrenic-based formulations. On a commercial basis, the polybromodiphenylalkane would be supplied to the formulation as a product predominant in the polybromodiphenylalkane selected. The product would have a form and an impurity content which would be characteristic of the process used to produce it. If the product's physical characteristics, e.g. thermal stability, limit the formulation's processability, then the processor's desire for the product is limited at best. If the product's color is not white or at least near white, the product will be suitable for use in some formulations, however, the product's use will not be acceptable in formulations calling for a white color.

Therefore, it is an object of this invention to provide a process for producing a product predominant in decabromodiphenylalkane which has good physical characteristics. It is also an object of this invention to provide a process for producing a product which not only has good physical characteristics but which also exhibits at least a near-white color. It is a further object of this invention to provide a formulation containing such decabromodiphenyl alkane products. A still further object of this invention is to provide articles made from such formulations.

THE INVENTION

This invention relates to a process for preparing a product which is predominant in decabromodiphenyl alkane. The product has good physical and color characteristics and is a flame retardant in formulation with normally flammable macromolecular materials.

The process comprises: forming a stirrable reaction mass by feeding a solution containing methylene bromide and diphenylalkane to a reaction vessel containing elemental bromine ($Br_2$) and a bromination catalyst; maintaining the reaction mass for a period of time sufficient to achieve perbromination of substantially all of the diphenylalkane; and recovering from the reaction mass the product which is predominant in decabromodiphenyl alkane.

The diphenylalkane solute portion of the feed solution can be represented by the formula:

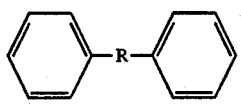

wherein R is an alkylene group containing 1 to 10 carbon atoms. Preferred R groups are methylene and ethylene, which give the preferred reactants, diphenyl- methane and 1,2-diphenylethane. Exemplary of other diphenylalkanes are: 1-methyl-1,2-diphenylethane, 1,4-diphenylbutane, 1,6-diphenylhexane, 2,3-dimethyl-1,4-diphenylbutane, 2,ethyl-3-methyl-1,4-diphenylbutane, 2-methyl-1,7-diphenylhexane, 1,9-diphenylnonane and 1,10-diphenyldecane. The diphenylalkane reactant can be produced by various routes. For example, CA 97 38651d (Japanese Kokai 82/45114) and CA 46 7084g disclose the reaction of benzene and ethylene dihalide in the presence of aluminum trichloride to yield diphenylalkane.

Another process for producing diphenylalkane includes the oxidative dimerization of toluene at a temperature of at least 400° C. in the presence of a metal oxide catalyst to yield diphenylethane and diphenylalkene. The latter product is then hydrogenated to remove the olefinic unsaturation.

It is not uncommon for the diphenylalkane reactant to be accompanied by various impurities, especially isomeric impurities. These impurities often give the final decabromodiphenylalkane product an off color. Exemplary of these color-causing impurities are stilbene and 1,1-diphenylethane which often accompany 1,2-diphenylethane. Diminishing the impurity content can be accomplished in a conventional manner, for example, the diphenylalkane can be recrystallized. See Example XI wherein a recrystallization method is described.

The use of methylene bromide as a solvent portion of the feed solution is an important aspect of this invention, as its use gives a superior product. In Table I, which follows the Examples herein, the superior thermalstability of a diphenylalkane product of this invention is shown.

The feed solution generally contains from about 40 to about 90 wt. % methylene bromide. The use of much less methylene bromide, say about 35 weight percent, would yield a reaction mass which is difficult to stir unless a larger excess of $Br_2$ is used than is hereinafter specified. When methylene bromide quantities exceed the upper end of the above range, then process economics are adversely affected as the unneeded extra methylene bromide is an additional cost borne by the process. A preferred amount of methylene bromide is within the range of from about 40 to about 85 weight percent, with a most preferred amount being within the range of from about 55 to about 80 weight percent.

Commercial grades of $Br_2$ may be used in the process of this invention. Should the $Br_2$ contain impurities that would give the final product an off-color, then either the $Br_2$ must be treated to reduce its impurity content or the off-color product must be treated to improve its color. The $Br_2$ is conveniently treated by simple distillation techniques. The off-color product can be treated by washing it with an organic wash solvent after the product is recovered from the reaction mass but prior to its being oven aged. The organic wash solvent can be methylene bromide, ethylene dichloride, carbon tetrachloride, xylene, toluene, benzene, acetone, methanol, etc. Methylene bromide is preferred since it is the same compound used as the solvent in the process.

The catalyst used in the process of this invention is preferably $AlCl_3$ and/or $AlBr_3$, although use may be made of aluminum powder, iron powder, $FeCl_3$ and/or $FeBr_3$, alone or in combination with the aluminum trihalide(s). Other bromination catalysts are suitable provided that they have sufficient catalytic activity to provide for perbromination under the process conditions which will be encountered. Catalytic quantities are used. Typically, catalysts will be present in an amount within the range of about 0.1 to about 20 weight percent based on the weight of the diphenylalkane reactant used in the process. A preferred amount is within the range of from about 1 to about 10 weight percent on the same basis.

During the addition of the feed solution to the reaction vessel, the temperature of the reaction mass should be at least about 5° C. A preferred temperature range is from about 10° C. to about 40° C. Most conveniently, the reaction mass can initially be at room temperature (20° C. to 40° C.) and under an atmospheric process pressure. If it is desired to achieve a reaction mass temperature above about 50° C., then provision should be made to prevent or reduce $Br_2$ and or methylene bromide losses from the reaction mass. This can be achieved by increasing the process pressure to prevent boiling or by providing for refluxing of volatilized $Br_2$ and/or methylene bromide as required.

The feed solution addition will generally occur over a period of time and the addition rate is dependent upon the scale of the reaction and the ability to control the temperature and to handle hydrogen bromide evolution. On a laboratory scale, the addition typically requires about 0.5 to about 1.5 hours while on a commercial scale, the addition could involve about 1.0 to about 10.0 hours or longer. Four to five hours would be typical for the commercial scale.

After the addition is complete, the reaction mass is maintained for at least the period of time needed to insure substantial perbromination of the diphenylalkane in high yields. It is preferred that, during this maintenance, the reaction mass temperature be above about 50° C. to minimize maintenance time. While such elevated temperatures are useful, care must be taken not to unduly diminish the $Br_2$ and/or methylene bromide content of the reaction mass by irretrievably boiling the $Br_2$ and/or the methylene bromide from the reaction mass. To prevent such diminishment, the process temperature and pressure can be coordinated so that the $Br_2$ and methylene bromide boiling points are not reached. A more preferred technique is to allow a boiling condition and to provide for refluxing of the evolving vapors back to the reaction mass. Under a preferred pressure, which is about atmospheric, the temperature, at reflux, will be within the range of from about 60° C. to about 80° C. The maintenance time at a temperature within this range will be at least about 2.5 hours.

The amount of $Br_2$ initially present in the reaction vessel should provide at least a 10% excess above the stoichiometric amount needed to produce the desired decabromodiphenyl ethane product. The temperature of the reaction mass during the maintenance period and the amount of catalyst used will influence the amount of $Br_2$ that is preferably used as a larger excess is beneficial at the lower maintenance temperatures or catalyst amount while a smaller excess is sufficient at higher maintenance temperatures or catalyst amounts. For example, at a maintenance temperature of about 50° C., the excess should be about 150%, while, at maintenance temperature of about 80° C., the excess can be about 100%. Amounts of $Br_2$ much less than 50% excess will result, at the lowest maintenance temperatures, in a probability of obtaining an under-brominated product. The stoichiometric amount of $Br_2$ is defined as that amount of $Br_2$ needed to provide one Br atom for each substitution site and one Br atom for the attendant formation of HBr which accompanies such substitution. Thus, the stoichiometric amount provides one mole of $Br_2$ per substitution site. By example, decabromodiphenyl ethane formation will, stoichiometrically, require 10 moles of $Br_2$ to achieve the desired substitution.

After the maintenance period is complete, the product which is predominant in decabromodiphenyl alkane is recovered from the reaction mass. Recovery can be by any conventional technique. Preferably, the reaction mass is allowed to cool to room temperature. Water is then added to deactivate the catalyst. Subsequently, the reaction mass is heated to drive off the bromine and methylene bromide still present. After such has been achieved, the product is filtered from the reaction mass and is washed with water to reduce the presence of deactivated catalyst and other impurities. After solvent washing, the product is dried at a temperature of from about 140° C. to about 170° C. for one hour. The product is then stored or immediately oven aged to further remove entrained $Br_2$, solvent and other impurities. The oven aging generally will occur at a temperature in excess of 150° C., but below 275° C., for a period of about 4 to about 24 hours.

The decabromodiphenyl alkane product of this invention, as before noted, has good color and physical characteristics. The product, after oven aging, exhibits high purity and high thermal stability—indeed, the decabromodiphenyl ethane product of this invention exhibits a melting point within the range of from about 344° C. to about 355° C. and a weight loss less than about 20 weight percent at 400° C. when subjected to thermogravimetric analysis and has a weight loss profile as follows,

|  | 300° C. | 350° C. | 400° C. |
|---|---|---|---|
| Percent Weight Loss | <0.5 | <4.5 | <20.0 |

The color of the decabromodiphenyl alkane product of this invention is at least near-white. For example, the decabromodiphenyl ethane product can have the following Hunter Colorometer values, L=94 to 95, a=0 to 0.3, b=5 to 6 and Y.I.=10 to 12.

The decabromodiphenyl alkane predominant product of this invention may be used as a flame retardant in formulation with virtually any flammable material. The material may be macromolecular, for example, a cellulosic material or a polymer. Illustrative polymers are: olefin polymers, cross-linked and otherwise, for example, homopolymers of ethylene, propylene, and butylene; copolymers of two or more of such alkylene monomers and copolymers of one or more of such alkylene monomers and any other copolymerizable monomers, for example, ethylene/propylene copolymers, ethylene/ethyl acrylate copolymers and ethylene/vinyl acetate copolymers; polymers of olefinically unsaturated monomers, for example, polystyrene, e.g. high impact polystyrene, and styrene copolymers; polyurethanes; polyamides; polyimides; polycarbonates; polyethers; acrylic resins; polyesters, especially poly(ethyleneterephthalate) and poly(butyleneterephthalate); epoxy resins; alkyls; phenolics; elastomers, for example, butadiene/styrene copolymers and butadiene/acrylonitrile copolymers; terpolymers of acrylonitrile, butadiene and styrene; natural rubber; butyl rubber; and polysiloxanes. The polymer may also be a blend of various polymers. Further, the polymer may be, where appropriate, cross-linked by chemical means or by irradiation.

The amount of the product of this invention used in a formulation will be that quantity needed to obtain the flame retardancy sought. It will be apparent to those skilled in the art that for all cases no single precise value for the proportion of the product in the formulation can be given, since this proportion will vary with the particular flammable material, the presence of other additives and the degree of flame retardancy sought in any given application. Further, the proportion necessary to achieve a given flame retardancy in a particular formulation will depend upon the shape of the article into which the formulation is to be made, for example, electrical insulation, tubing and film will each behave differently. In general, however, the formulation may contain from about 5 to about 40 wt. %, preferably 10 to 30 wt. %, of the product when it is the only flame retardant compound in the formulation.

It is especially advantageous to use the product of this invention with an inorganic compound, especially ferric oxide, zinc oxide, zinc borate, the oxide of a Group V element, for example, bismuth, arsenic, phosphorus and especially antimony, in the formulation. Of these compounds, antimony oxide is especially preferred. If such a compound is present in the formulation, the quantity of decabromodiphenyl alkane predominant product needed to achieve a given flame-retardancy is accordingly reduced.

Formulations containing a flame retardant system comprised of the product of this invention and the above inorganic compounds may contain up to about 40% by weight of the system, preferably between 20% and 30% by weight.

It is believed that the product of this invention and the inorganic compound will react under the conditions of combustion of a flammable material to form inorganic bromine compounds, e.g., hydrogen bromide and metal oxybromides, which assist in retarding combustion. The bromine-bearing product of this invention also acts as a flame retardant independently and the proportions of the product and inorganic compound in a flame retardant system are a matter of choice, depending on the material in which the system is to be incorporated and commercial considerations. Generally, the product of this invention and the inorganic compound are in a weight ratio of from about 1:1 to about 7:1, and preferably of from about 2:1 to about 4:1.

The formulations containing the product of this invention may contain any of the additives usually present in such formulations, e.g. plasticizers, antioxidants, fillers, pigments, UV stabilizers, etc.

Thermoplastic articles formed from formulations containing a thermoplastic polymer and a product of this invention can be produced conventionally, e.g. by injection molding, extrusion molding, compression molding, and the like.

The following examples are presented.

EXAMPLE I

This example is not of the invention but rather is presented for comparative purposes. The process illustrated by this example produces a product predominant in decabromodiphenyl ethane using bromine as both a reactant and as the sole solvent.

A 3-L resin kettle was equipped with a mechanical stirrer, a thermometer, a temperature controller, an addition funnel wrapped with a heating tape, a heating mantle and a double reflux condenser. The kettle was charged with 2407.0 g (15.00 moles) of bromine and 8.9 g of anhydrous aluminum chloride. The amount of bromine charged represents an amount which is a 150% excess of the stoichiometric amount needed to perbrominate the diphenylethane reactant.

The addition funnel was charged with ground diphenylalkane (111.0 g, 0.61 moles) and heated slowly by way of the heating tape to provide molten diphenylethane (55° C.-66° C.). The molten diphenylalkane was added to the reactor over a period of 60 to 75 minutes. The resultant reaction mass during this addition was kept at a temperature from 25° C. to 30° C.

After the addition was substantially complete, the reaction mass was stirred and heated to reflux (60° C.) for 4.5 hours. After this period, the reaction was deemed complete.

Water (1 L) was added to the reaction mass to deactivate the catalyst. Bromine was then distilled off until the vapor obtained had a temperature of 100° C. indicating that substantially all of the bromine was removed.

The resultant solid product was filtered, washed once with water and then with 250 mL xylene. This washed product was dried and then oven aged at 200° C. for 16 hours, to yield 572.0 g (96%) of a product predominant in decabromodiphenyl ethane. The product had a melting point of 340° C.-344° C. and a bromine content of 82.7%.

EXAMPLE II

This example is presented for comparative purposes and is not of this invention. The process illustrated by this example produces a product predominant in decabromodiphenyl ethane by using ethylene dichloride as a solvent in the process.

In a glass reaction vessel was placed 256 g (1.6 moles) of bromine, 25 mL of ethylene dichloride and 1.5 g of anhydrous aluminum chloride. While stirring, a solution of 14.6 g (0.08 moles) of diphenylethane in 25 mL of ethylene dichloride was added at 25° C.-35° C. over a 2-hour period. The reaction mixture was heated to reflux and refluxed for 6 hours. It was then cooled to room temperature and 150 mL of ethylene dichloride added. Bromine was distilled out along with some ethylene dichloride. The mixture was cooled and another 100 mL of ethylene dichloride was added and bromine was again distilled off until only a trace of bromine color remained. The product was recovered by filtration, washed twice with ethylene dichloride and dried at 100° C. for 4 hours to give 76.2 g (98.5% yield) of a light orange product predominant in decabromodiphenyl ethane. The product was oven aged at 200° C. for 16 hours to give an off-white material having a melting point of 335° C.-342° C. and a bromine content of 82.1% (calculated=82.1%).

EXAMPLE III

This example is presented for comparative purposes and is not of this invention. The process illustrated produces a product predominant in decabromodiphenyl ethane by adding $AlCl_3$ catalyst to a mix of bromine, methylene bromide and diphenylalkane.

To a 3-L resin kettle fitted with a mechanical stirrer, a thermometer, a temperature controller, an additional funnel, a heating mantle and a double reflux condenser was added 320 g (2.0 moles) of $Br_2$. The $Br_2$ was stirred while a solution of 20 mL of methylene bromide and 18.2 g (0.1 mole) of recrystallized diphenylalkane was added to the kettle. The diphenylalkane and the methylene bromide were obtained from Aldrich Chemical Co., Inc. The diphenylalkane had been recrystallized in the manner illustrated in Example XI. The addition occurred over 20 minutes and the temperature rose from 25° C. to 29° C. A moderate reaction was seen within 5 minutes of the addition.

After the addition had been completed (0.4 g) of anhydrous $AlCl_3$ was added to the vessel. Vigorous reaction was seen. After 3 minutes an additional 0.5 of anhydrous $AlCl_3$ was added. Again, the reaction was vigorous. The two additions brought the temperature up to 30° C. A third addition (0.5 g) and a fourth addition (0.6 g) of anhydrous $AlCl_3$ followed. These additions were separated by 3 minutes. The reaction mixture was heated to reflux (65° C.) and maintained at reflux for 6 hours. The temperature at the end of the reflux period was 68° C. The reaction mixture was allowed to cool to 50° C. Water (200 mL) was added to deactivate the catalyst. The reaction mixture was allowed to stand overnight.

The reaction mixture was then heated to distill off the remaining $Br_2$ and methylene bromide to a vapor temperature of 100° C. The remaining material was cooled and filtered by the application of suction through a sintered glass funnel. The recovered solid decabromodiphenyl ethane predominate product was washed twice with 150 mL of water. After washing, the product was dried in an oven at 100° C. for 3 hours. The dried product was then oven-aged at 200° C. for 18 hours. After oven-aging the product was washed 3 times with 100 mL toluene for each washing. The washed product was then dried in an oven at 190° C. for 3 hours.

The decabromodiphenyl ethane predominate product weight for 93.5 g and was dark tan. The Hunter color values and the TGA values in Table II for this Example were for product which had been oven-aged but not washed with toluene and dried.

EXAMPLE IV

This example is presented for comparative purposes and is not of this invention. The process illustrated is an attempt to produce a product containing decabromodiphenyl ethane via a process described in U.S. Pat. No. 3,763,248.

The apparatus used in Example III was used in this Example. To the kettle was added 18.2 g (0.1 mole) of diphenylalkane and 40 mL of methylene bromide. The recrystallized diphenylalkane was obtained from Aldrich Chemical Co., Inc. and had been recrystallized by the method of Example II. The vessel contents were stirred as 62 mL of $Br_2$ was added dropwise in about 10 minutes. When 20 mL of $Br_2$ had been added, a rapid reaction was observed. Upon completion of the $Br_2$ addition, the temperature of the kettle contents had risen from 21° C. to 30° C.

$AlCl_3$ (0.4 g, 0.0029 mole) in methylene bromide (48 mL) was added to the kettle over a period of 5 minutes. The reaction temperature rose from 25° C. to 30° C. and vigorous reaction was observed.

The vessel contents were heated to 83° C. and a moderate reflux was noted. At this temperature, the vessel content was stirred for 3 hours. After this period, unreacted bromine was clearly visible. No solids were seen.

The reaction contents were cooled to 25° C. Anhydrous $AlCl_3$ (0.5 g, 0.0037 mole) was added to the kettle. Another portion of anhydrous $AlCl_3$ (0.7 g, 0.0052 mole) was added. A moderate reaction was observed. (Total $AlCl_3$ added =0.0118 moles, =0.01 mole per mole $Br_2$).

The vessel contents were then heated to 87° C. and stirred for 1.5 hours. During this period all bromine had disappeared. The vessel contents were in the form of a slurry. To the slurry was added 50 mL of methylene bromide followed by 10 percent HCl (100 mL). The slurry was stirred vigorously for 5 minutes. After stirring organic and aqueous layers were formed. The organic layer was thick and cream-colored.

The organic layer was recovered with a separating funnel and washed twice with 100 mL of 5 percent aqueous NaOH. An organic layer formed again and was separated from the aqueous layer. The organic layer was concentrated on a rotary evaporator at 95° C. for one hour. A cream-colored solid was obtained which weighed 95.0 g (97.7 percent yield). Due to sticking, however, only 91.3 g of the solid was recovered.

The recovered product was further dried in an oven at 100° C. for 2 hours. The dried product was ground well and had a creamy yellow color. Attempts to oven-age this product at 200° C. for 3 to 4 hours resulted in the product turning very dark and showing signs of decomposition. Other properties of the product are given in Table II.

The following Examples illustrate features of this invention.

EXAMPLE V

A 500-mL-resin kettle was equipped with a mechanical stirrer, reflux condenser, a thermometer, a temperature controller and an addition funnel.

The kettle was charged with 320 g of $Br_2$ (2.0 moles) and 1.8 g of aluminum chloride. The 320 g of bromine represents a 100% excess of bromine beyond the stoichiometric amount required for perbromination.

The addition funnel was charged with a solution containing 18.2 g diphenylethane (0.1 mole) and 49.4 g of methylene bromide (20 mL). The solution was added via the funnel dropwise into the kettle over a period of 30 minutes. During the addition, the resultant reaction mass was stirred at room temperature. After the addition was complete, the reaction mass was stirred and heated to reflux (65° C.-67° C.) for 6 hours.

After the 6-hour period had lapsed, the reaction was deemed complete and the reaction mass was cooled to room temperature. Water (150 mL) was added to the reaction mass to deactivate the catalyst. After catalyst deactivation the reaction mass was heated to remove bromine and methylene bromide still present until the vapor obtained was approximately at 100° C.

The solid product was filtered from the remaining solution and washed twice with 100-mL-portions of water and dried at 160° C. for one hour. The product was then oven aged at 200° C. in a forced-air oven for 15 hours. A white product (95.5g, 98%) was obtained. The product had a melting point of 344° C.-354° C. and an average bromine content of 82.6%.

EXAMPLE VI

A resin kettle (3L) was equipped with a mechanical stirrer, reflux condenser, a thermometer with a temperature controller and an addition funnel.

The kettle was charged with 2160 g of $Br_2$ (13.5 moles) and 10.9 g of anhydrous aluminum chloride. The amount of $Br_2$ used in this example represents an 80% excess of Br$_2$ beyond the stoichiometric amount required for perbromination.

The addition funnel was charged with a solution containing 136.8 g diphenylalkane (0.75 mole) and 185.2 g of methylene bromide (75 mL). The solution was added via the funnel dropwise into the kettle over a period of 95 minutes. During the addition, the resultant reaction mass was stirred at room temperature. After the addition was complete, the reaction mass was stirred and heated to reflux (65° C.-66° C.) for 5 hours.

After the 5-hour period had lapsed, the reaction was deemed complete and the reaction mass was cooled to room temperature. Water (800 mL) was added to the reaction mass to deactivate the catalyst. After deactivation of the catalyst, the reaction mass was heated to remove bromine and methylene bromide still present. The heat was removed when the vapor was at 100° C.

The solid decabromodiphenyl ethane predominant product was filtered from the reaction mass and washed twice with 250-mL-portions of water and then twice with 250-mL-portions of xylene. The recovered product was dried in air at room temperature overnight. The product was then oven aged at 200° C. in a forced-air oven for 12 hours. A light tan product (719.8 g, 98.7%) was obtained. The product had a melting point of 340° C.-350° C., and a bromine content of 83.3%.

EXAMPLE VII

The procedure of Example III was followed except that 30 mL (74.4 g) of methylene bromide was used to dissolve 18.2 g of diphenylalkane (18.2g) and the recovered product was oven aged for 16 hours at 200° C.

An off-white predominantly decabromodiphenyl ethane product (93.0 g, 95.6%) was obtained. This product had a melting point of 345° C.-354° C. and a bromine content of 83.4%.

EXAMPLE VIII

A 3-L resin kettle was equipped with a mechanical stirrer, reflux condenser, an addition funnel, a thermometer with a temperature controller and a heating mantle. The kettle was charged with 1600 g of bromine (10 moles, 100% excess of stoichiometric) and 9.0 g of anhydrous aluminum chloride.

The addition funnel was charged with a solution containing 91.0 g diphenylalkane (0.5 mole) and 185 g of methylene bromide (75 mL). The solution was added to the kettle over a period of 40 minutes.

After the addition was complete, another 62.0 g of methylene bromide (25 mL) was added to aid in the stirrability of the reaction mass. The reaction was then heated to 66° C.-67° C. and stirred at that temperature for 6 hours.

After the 6-hour period had lapsed, the reaction mass was cooled to 50° C. Water (500 mL) was added to the reaction mass to deactivate the catalyst. The reaction mass was then heated to remove the Br$_2$ and methylene bromide therefrom. After this removal was effected, the white product was filtered from the reaction mass.

The white product, which was predominantly decabromodiphenylalkane, was washed twice with 400-mL portions of water. After this washing, the recovered product was dried at 125° C. for 2 hours. After drying, the product was oven aged at 200° C. for 8 hours in a forced-air oven.

After the oven aging was effected the product was washed twice with 400-mL portions of toluene and then dried at room temperature. After drying, the product was again heated at 200° C. for another 2 hours to remove any solvent which may be still present.

The final yield of the product was 475.4 g (97.8%). The final product was subjected to thermogravimetric analysis and had a 0.0 weight percent loss at 200° C. and 300° C., a 17.0 weight percent loss at 400° C. and a 84.9 weight percent loss at 500° C.

The final product was also tested for color with a Hunter Colorometer which gave the following values: L=91.5, a=0.3, b=9.98, and Y.I.=20.0.

The final product also had a melting point of 344° C.-352° C.

EXAMPLE IX

A portion of the final product produced in Example VI was formulated with Huntsman 840D HIPS (High Impact Polystyrene) and antimony oxide synergist. The decabromodiphenyl ethane predominant product was present in an amount of about 12 weight percent while the antimony oxide synergist was present in an amount of about 4 weight percent. All weight percents were based upon the total weight of the formulation.

The formulations were made by extrusion on a Haake System Forty Extruder at 205° C.-225° C. The recovered formulation was then injection molded on a Battenfeld injection molder at a zone temperature of 200° C.-227° C.

The injection molded articles were tested in accordance with UL 94 and ⅛-inch strips gave a rating of V-0. Further, the injection molded articles were subjected to tests for determination of UV stability. A ΔE48(Sunlighter) of 28.5 was obtained.

EXAMPLE X

A 1-L resin kettle fitted similarly to the 3-L resin kettle in Example VI was used. To the kettle was added 315 mL (6.1 moles) of Br$_2$ and 5.4 g of anhydrous AlCl$_3$. While the kettle contents were being stirred, 54.6 g (0.3 mole) of recrystallized diphenylalkane and 60 mL of methylene dibromide was added to the kettle over 34 minutes. The kettle content rose in temperature from 25° C. to 40° C. The kettle contents were strongly agitated and heated to reflux (65°-66° C.) for 2.5 hours. After this reflux period the kettle contents were cooled to 45° C. and 450 mL of water was added thereto.

Subsequent to the water addition the remaining Br$_2$ and methylene dibromide was distilled off. As the distillation was occurring, solid product settled in the bottom along the sides of the flask and was seen to be caking. Agitation was increased. Initially no effect was seen but when the vapor temperature reached 65° C., the cake broke and a nice slurry formed.

After the distillation the solid decabromodiphenyl ethane product was filtered and washed with water (150 mL) twice. The washed product was dried at 100° C. for 3 hours in an air oven. The dried product was then oven-aged at 190° C. for 18 hours to give an off-white product, 286.3 g which represents a 98.2% yield.

The oven-aged product was then washed 3 times with 150 mL of toluene and then dried at 190° C. for 3 hours. The final product weighed 284.6 g (97.6% yield). Its color was white. The product also had the Hunter color values and the TGA values shown in Table II.

EXAMPLE XI

The following example illustrates a method for purifying diphenylethane reactant to obtain a good color.

A 1-L beaker was charged with methanol (300 mL). Crude diphenylethane (300 g) was then added. The contents of the beaker were heated and stirred at 65° C., and the resulting clear solution was then allowed to cool slowly to room temperature. A crystalline solid was formed. The solid was filtered and washed once with 120 mL methanol and then dried. The recovery was 274.5 g (91.5%). The recrystallized material had a melting point of 50° C.-54° C. which is slightly higher than the 49° C.-50° C. for the original starting diphenylethane. The starting diphenylethane had a Yellowness Index of 33.2 (L=81.2, a=−2.9, b=16.1) while the recrystallized diphenylethane material had a Yellowness Index of 2.8. (L=90.8, a=−0.4, b=1.4).

It is believed that the diphenylethane reactant should have a Yellowness Index of 5 or less as measured by the Hunter Colorometer so that the product predominant in decabromodiphenyl ethane will have a good color.

The following Tables illustrate the superior thermal stability and color of the product of the process of this invention.

TABLE I

THERMOGRAVIMETRIC ANALYSIS

| Sample | Percent Weight Loss at | | | | |
|---|---|---|---|---|---|
| | 300° C. | 350° C. | 400° C. | 450° C. | 500° C. |
| From Example I (not of the invention) | 0.8 | 5.3 | 28.3 | 79.6 | 99.6 |
| From Example V (of the invention) | 0.4 | 3.5 | 14.6 | 61.6 | 91.4 |
| From Example VI (of the invention) | 0.4 | 3.1 | 15.9 | 71.3 | 91.5 |

| Sample | Percent Weight Loss at | | | |
|---|---|---|---|---|
| | 320° C. | 357° C. | 375° C. | 395° C. |
| From Example II (not of the invention) | 2.0 | 5.0 | 10 | 25 |

TABLE II

| | Melting Point | Hunter Color Values | | | | TGA Percent Weight Loss at | | | | |
|---|---|---|---|---|---|---|---|---|---|---|
| | | L | a | b | Y.I. | 100° C. | 200° C. | 300° C. | 400° C. | 500° C. |
| Example III (not of this Invention) | 336–348° C. | 76.3 | 2.5 | 11.9 | 30.5 | 0.09 | 0.11 | 0.34 | 11.9 | 90.9 |
| Example IV (not of this Invention) | 264–284° C. | 87.0 | −1.6 | 22.5 | 45.1 | 0.20 | 0.66 | 1.63 | 16.6 | 77.0 |
| Example X (of this Invention) | 344–348° C. | 92.1 | 0.1 | 7.5 | 15.0 | 0.0 | 0.0 | 0.4 | 19.4 | 89.7 |

All thermogravimetric analyses were performed in the presence of air and with a DuPont Model 990 Thermal Analyzer, equipped with a Model 951 TGA Module.

A typical measurement was performed by placing 10–20 mg of the material to be tested in the platinum sample holder, followed by enclosing the sample holder in a quartz tube. The entire assembly was then inserted into the furnace, and the air flow was adjusted to 50 mL/min. The system was programmed to run from 25° C. to 500° C. at a heating rate of 10° C. per minute. The weight loss vs. temperature was recorded automatically by the instrument.

The Hunter Color values were obtained with a Lab Scan II colorometer produced by Hunter Lab of Reston, Virginia. The Y.I values were obtained by ASTM D 1925.

As can be seen from the Tables, the decabromodiphenyl ethane predominate product of this invention is superior in that it exhibits both good stability and color. Only Example III, shows similar stability at temperatures above 300° C., though it is inferior at temperatures from 100° C. and 200° C.

What is claimed:

1. A thermoplastic formulation comprising:
   (a) a flammable macromolecular material; and
   (b) a flame retardant amount of a decabromodiphenylethane product containing a predominate amount of decabromodiphenylethane and a lesser amount of impurities, said decabromodiphenylethane being produced by the bromination of diphenylethane, and said decabromodiphenylethane product being oven-aged and thereafter having a melting point within the range of from about 344° C. to about 355° C.

2. The thermoplastic formulation of claim 1 wherein the flammable macromolecular material is high impact polystyrene.

3. The thermoplastic formulation of claim 1 wherein the flammable macromolecular material is acrylonitrile butadiene-styrene.

4. The thermoplastic formulation of claim 1 wherein the flammable macromolecular material is a polyolefin.

5. A thermoplastic formulation comprising:
   (a) a flammable macromolecular material; and
   (b) a flame retardant amount of a decabromodiphenylethane product of decabromodiphenylethane and a lesser amount of impurities, said decabromodiphenylethane being produced by the bromination of diphenylethane, and said decabromodiphenylethane product being oven-aged and thereafter exhibiting a weight loss of less than about 20 wt. % at 400° C. when subjected to thermogravimetric analysis.

6. The thermoplastic formulation of claim 5 wherein the flammable macromolecular material is high impact polystyrene.

7. The thermoplastic formulation of claim 5 wherein the flammable macromolecular material is acrylonitrile butadiene-styrene.

8. The thermoplastic formulation of claim 5 wherein the flammable macromolecular material is a polyolefin.

9. A thermoplastic formulation comprising:
   (a) a flammable macromolecular material; and
   (b) a flame retardant amount of a decabromodiphenylethane product containing a predominate amount of decabromodiphenylethane ethane and a lesser amount of impurities, said decabromodiphenylethane being produced by the bromination of diphenylethane, and said deecabromodiphenylethane product being oven-aged and thereafter having the following weight loss profile when subjected to thermogravimetric analysis,

| | 300° C. | 350° C. | 400° C. |
|---|---|---|---|
| Percent Weight Loss | <0.5 | <4.5 | <20.0 |

10. The thermoplastic formulation of claim 9 wherein the flammable macromolecular material is high impact polystyrene.

11. The thermoplastic formulation of claim 9 wherein the flammable macromolecular material is acrylonitrile butadiene-styrene.

12. The thermoplastic formulation of claim 9 wherein the flammable macromolecular material is a polyolefin.

* * * * *